(12) United States Patent
Huber et al.

(10) Patent No.: US 8,030,589 B2
(45) Date of Patent: Oct. 4, 2011

(54) METHOD FOR DETECTING AND SORTING GLASS

(75) Inventors: Reinhold Huber, Fürstenfeld (AT); Christian Pansinger, Graz (AT)

(73) Assignee: Binder + Co AG, Gleisdorf (AT)

( * ) Notice: Subject to any disclaimer, the term of this patent is extended or adjusted under 35 U.S.C. 154(b) by 466 days.

(21) Appl. No.: 11/500,840

(22) Filed: Aug. 8, 2006

(65) Prior Publication Data

US 2007/0029233 A1    Feb. 8, 2007

(30) Foreign Application Priority Data

Aug. 8, 2005  (AT) ................. GM539/2005

(51) Int. Cl.
*B07C 5/00* (2006.01)
(52) U.S. Cl. ........................ 209/578; 209/522
(58) Field of Classification Search ............ 209/522, 209/523, 524, 576, 577, 578
See application file for complete search history.

(56) References Cited

U.S. PATENT DOCUMENTS

| | | | |
|---|---|---|---|
| 3,097,744 A | | 7/1963 | Hutter et al. |
| 4,830,192 A | * | 5/1989 | Plester et al. ............... 209/3.1 |
| 5,260,576 A | * | 11/1993 | Sommer et al. ............ 250/359.1 |
| 5,419,438 A | * | 5/1995 | Squyres et al. .............. 209/3.1 |
| 5,663,997 A | * | 9/1997 | Willis et al. .................. 378/45 |
| 5,799,105 A | * | 8/1998 | Tao .............................. 382/167 |
| 6,504,124 B1 | * | 1/2003 | Doak ........................... 209/581 |
| 7,081,594 B1 | * | 7/2006 | Khalfan et al. .............. 209/578 |
| 7,639,352 B2 | | 12/2009 | Huber et al. |

FOREIGN PATENT DOCUMENTS

| | | |
|---|---|---|
| DE | 43 39 822 | 11/1993 |
| DE | 43 01 988 | 7/1994 |
| DE | 43 39 822 | 5/1995 |
| EP | 0 426 893 | 5/1991 |
| EP | 0 550 944 | 7/1993 |
| EP | 0 820 819 | 1/1998 |
| GB | 1 221 363 | 2/1971 |
| GB | 2 251 305 | 7/1992 |
| JP | 2000338046 | 12/2000 |
| JP | 2004275855 | 10/2004 |
| JP | 2004305965 | 11/2004 |
| JP | 2005181075 | 7/2005 |
| WO | WO 2004/063729 | 7/2004 |
| WO | WO 2005/016835 | 8/2004 |

OTHER PUBLICATIONS

European Search Report + English translation Nov. 15, 2006.
Austrian Search Report + English translation Jan. 4, 2006.

* cited by examiner

*Primary Examiner* — Joseph C Rodriguez
*Assistant Examiner* — Kalyanavenkateshware Kumar
(74) *Attorney, Agent, or Firm* — Collard & Roe, P.C.

(57) ABSTRACT

A cost efficient and reliable method for online sorting of special glass which works independent of the color of glass and the shape of the material. The scrap glass stream to be detected is thereby irradiated by UV absorption or transmission values of the scrap glass stream, more specifically of the material-specific UV absorption edges and "UV-cutoff" frequencies, with reference values obtained before from standardized material laboratory inspections. If special glass is being detected, blowing nozzles disposed downstream of a detector unit divert the special glass toward a predetermined location where it is deposited. There can also be a system which includes a radiation source, a detection unit, an evaluation and control unit and a removal apparatus.

17 Claims, 3 Drawing Sheets

METHOD FOR DETECTING AND SORTING GLASS

CROSS REFERENCE TO RELATED APPLICATIONS

Applicant claims priority under 35 U.S.C. §119 of Austrian Patent Application Serial No. GM 539/2005 filed on Aug. 8, 2005 the disclosure of which is hereby incorporated herein by reference.

BACKGROUND OF THE INVENTION

The invention relates to a method for detecting and sorting glass in a scrap glass stream, preferably a stream of broken glass, wherein light rays emitted from a radiation source traverse the scrap glass stream and impinge on a detector unit. These light rays are processed by an evaluation and control unit in data communication therewith, the evaluation and control unit connected to the detector unit activating, as a function thereof, a removal apparatus such as a blowing nozzle. This nozzle is disposed downstream of the detector unit. This removal apparatus is for singling out undesired matter entrained in the scrap glass stream and diverting it to a predetermined location.

The recycling of scrap and broken glass together with an organized collection and selection method has been successfully practiced for quite a long time and has been capable of significantly reducing the energy expenditure in the industrial production of glass utensils. The known difficulty that the consumers collecting scrap glass are not very careful in separating the material with respect to color and to materials other than glass such as ceramics, stone, porcelain, could in the meantime be reliably overcome using automated material selecting methods with opto-electronically controlled sorting apparatus.

For the purpose of sorting colors and for detecting foreign material, methods of contactless measurement by means of infrared or RGB sensors are utilized most of the time. These sensors induce the removal of undesired foreign material from the scrap glass stream or the diversion of colored glass into fractions intended therefore by means of blowing or aspirating nozzles, using therefore the recorded degree of light transmission or absorption of the light directed onto the scrap glass stream.

An issue that heretofore was of minor importance in glass scrap but is gaining prominence lately is the detection of special glass in the scrap glass stream. Special glasses refer to glass types specially created for specific applications and having chemical and physical properties strongly differing from those of normal glass (lime-natron glass), more specifically having a substantially higher melting point and also improved thermal properties. They include glass-ceramics, fused silica glass, lead glass as well as temperature and heat-shock resistant technical glasses such as borosilicate glasses.

Not only in the industry, but in private households as well, there is a need for heat-resistant glass having improved thermal properties and being heat-shock resistant as well. While normal glass already undergoes chemical reactions at about 1,400° C. and melts at about 1,500° C., some special glasses are still capable of approximately keeping their chemical structures in these temperature ranges and resist melting. Glass-ceramics and pure fused silica glass even have a melting point ranging from about 1,800 to 2,000° C. Technical glasses such as borosilicate glasses, which find application in electrical engineering and electronics as well as in optics, are found to be very resistant to heat, expansion and heat-shock.

The primary manufacturing process of special glass is similar to that of normal glass except that, depending on the application field, a certain amount of special oxides are added to the glass melt. A boron-silicate glass may contain about 7-13% of $B_2O_3$ and 2-7% of $Al_2O_3$ as an additive. Depending on the properties desired, either basic oxides (such as sodium, potassium, magnesium, calcium, barium or zinc oxide) or acidic oxides (such as boron trioxide, aluminium trioxide or diphosphorus pentoxide) are added during glass manufacturing, with metals such as copper, chromium, manganese and iron being utilized as the coloring agents. Boron-silicate glass is resistant to chemical substances and to heat and temperature shocks and find therefore application in the chemical industry, in laboratories, as ampoules and vials in the pharmaceutical industry but also in households such as in the form of cookware and light bulb carriers.

The production of glass-ceramics differs from usual glass manufacturing by an additional last method step. Since in normal glass production, the glass does not crystallize, crystallization nucleating agents such as TiO or $ZrO_2$ are added to the glass melt in order to cause the structure to crystallize when a molded glass body is heated anew. Accordingly, the material properties of glass-ceramics are similar to those of ceramics. Since the temperature expansion coefficient of glass-ceramics is equal to zero or even negative, this material is particularly suited for loads involving fast high-temperature changes and is for example used in the form of ceramic hot plates in households.

Lead glasses are another issue: although these glasses are very popular because they are highly refractive and can be readily surface-treated, they must imperatively be recycled in special glassworks where they are remolten under controlled conditions for environmental and health reasons.

It is precisely these described resistance properties of special glass, which are highly appreciated in the respective field of application, that cause considerable problems in the process of glass recycling as they prevent it from melting homogeneously into the normal glass in the crucible, thus disturbing the production process and leading to product flaws.

Some attempts have been made to allow for cost-effective online sorting of special glass. These are based on known methods in which the fractions are separated from the collected broken glass and substantially rely on opto-electronic systems which separate these fractions by means of color recognition in the range of visible light. This is achieved in that the piece that is to be singled out from the mixed scrap glass stream is irradiated from radiation sources while being conveyed on a sorting belt or while in free fall and the intensity of the radiation traversing the scrap glass stream or reflected therefrom is received by a detector unit and compared with reference values. An evaluation and control unit in data communication with the detector unit then associates the piece with a respective fraction and causes it to be grasped by pick-ups or to be diverted into predetermined containers by means of compressed air nozzles or aspirating nozzles.

Approaches exist in which the special glass is detected in the wavelength range of visible light by means of color classification means, mostly RGB sensors, which try to recognize a color from thresholds corresponding to already known special glass colors. Since special glasses mostly also have special shades such as violet or honeydew, this detection method allows for recognizing part of the special glass pieces without however providing for reliable detection of special glass. Since the staining guidelines for special glass are not standardized, some special glasses are also manufactured in conventional unimpressive colors such as white and brown so that they cannot be recognized. Glass in shades of brown in particular cannot be distinguished reliably, so that there is high glass loss because of erroneous sorting. A corresponding separating accuracy can only be generated conditionally since detection by color intensity comparison in the visible and infrared range depends inter alia on the thickness and the shape of the glass.

Other known methods for sorting special glass work with X-ray sensors where certain chemical components (e.g., aluminium oxide) of the special glass are excited by an X-ray source. The excited elementary particles or electrons react, emitting energy in the form of light the intensity of which is finally measured and evaluated for detection. The industrial market accepts this method using an X-ray sensor with reservation though since the utilization of X-rays always poses a certain health hazard to persons involved in the surroundings of the line because of the extremely short-waved radiation. Moreover, lines operating according to this method are of quite large construction and are costly throughout. This method does not ensure complete detection of special glasses, in particular not of some borosilicate glasses.

Another known method for sorting special glass works with the fluorescent property of special glass. Glass is thereby irradiated with UV light of a certain wavelength and starts fluorescing in a narrow visible spectral range since the irradiated light is partially absorbed by impurities present in the oxidic glass and is converted into fluorescence radiation. The color of this fluorescence radiation then allows drawing conclusions about the type of special glass. Such a method is known from DE 43 39 822 Cl for example. It has been found however that it is disadvantageous that the scrap glass stream is irradiated with UV light which depends on the special glass type to be sorted. Put another way, this means that the type of special glass contained in the scrap glass stream must be known before sorting in order to perform the radiation with UV light of the right wavelength.

Still another disadvantage is that the fluorescence effect described is typical for impurities contained in the special glass and not for the type of glass itself. Unwanted impurities or microinclusions in the furnace or cubicle material already occur during the manufacturing of glass, so that the fluorescence behavior is difficult to assess. Insofar the problem is that completely different kinds of special glass may have a comparable fluorescence spectrum and the same kind of special glass different fluorescence spectra. Another disadvantage of this method is that, because of the low concentration of impurities, a very strong light source must be utilized to excite them. This requires high energy expenditure and calls for the need of providing an edge filter for protecting the detector unit on the detector side.

SUMMARY OF THE INVENTION

It is therefore the object of the present invention to avoid these drawbacks and to provide a method for detecting and sorting special glass ensuring reliable and cost-efficient recognition of special glasses such as glass-ceramics, lead glass and temperature and heat-shock resistant technical glasses such as borosilicate glasses. These special glasses are intended to be detected and singled out from the scrap glass stream independent of the color and the coating thickness of the glass parts entrained in the scrap glass stream with no safety or health hazard to persons working in the surroundings of the sorting line.

One way to solve any object or problem is to provide a a method, wherein light rays emitted from a radiation source traverse a scrap glass stream consisting preferably of broken or scrap glass and impinge on a detector unit inside the stream, with their constitution being processed by an evaluation and control unit in data communication with the detector unit. Depending on this evaluation, the evaluation and control unit communicating with the detector unit activates a removal apparatus such as blowing nozzles which singles out unwanted material entrained in the scrap glass stream and diverts it toward a predetermined location.

In at least one embodiment, the scrap glass stream to be inspected can be irradiated by means of a radiation source the light of which is in the frequency range of UV light and that detection of the special glass is performed comparing the detected UV absorption or transmission values of the scrap glass stream with UV absorption or transmission values obtained from standardized material laboratory inspections, the wavelength range used for comparing the UV absorption or transmission values being the one in which the emitted light is absorbed. In the course of this comparison, the UV absorption edges ("cutoff" frequencies) actually obtained from the scrap glass stream sensed by the detector unit are processed and compared with reference values. The term UV absorption edges as used herein are understood to refer to that range of transmission values or of absorption value in which permeability no longer increases with decreasing wavelength.

It has been found, surprisingly, that, by virtue of their characteristic composition and amount of additives, special glasses such as glass-ceramics, lead glass or temperature and heat-shock resistant technical glasses such as borosilicate glasses have a clear material-specific absorption or transmission of impinging UV light, this allowing for reliable detection and sorting of these special glasses. In accordance with the method presented, the respective degree of UV transmission or absorption is evaluated algorithmically, being understood though that the reflected fraction of the UV light may be used for detecting special glass in equivalent fashion without departing from the idea of the invention.

The light emitted from the radiation source can cover the entire UV wavelength range. As a result, it is not necessary to know already before sorting which kind of special glass is contained in the scrap glass stream and needs to be sorted out.

In another embodiment the UV absorption or transmission values of the scrap glass stream detected by the detector unit are not compared across the entire wavelength range of the UV spectrum but only in selected wavelength ranges. These selected wavelength ranges are thereby determined using the absorption or transmission values obtained from sample pieces prior to sorting.

If the UV absorption or transmission values, are evaluated over the entire wavelength range of the UV spectrum, sorting may also be performed with reliable accuracy although this evaluating method involves an increased data volume that is to be processed.

There are provided a plurality of measurement points distributed over a choice of several defined wavelength ranges in order to acquire the UV absorption or transmission values, wherein these measurement points are always evenly spaced from each other. The measurement points may for example be provided spaced 30 nm apart. Application-specific distribution of the measurement points is intended to or is capable of ensuring complete acquisition of all the possibly occurring materials or special glasses.

Preferably the wavelength at which the light emitted from the UV radiation source ("UV cutoff" frequency) is completely absorbed or the wavelength range of almost complete absorption is preferably acquired to be able to draw conclusions about the nature of the material or the presence of special glass. In this respect, the range of UV absorption edge used comparing the UV absorption or transmission values with UV absorption or transmission values obtained before from standardized material laboratory inspections, the wavelength range used for comparing the UV absorption or transmission V values being the one in which the emitted light is absorbed, is the range in which the permeability of the piece from the scrap glass stream ranges from 0 to 50%. Those wavelengths in which the permeability of the piece from the scrap glass stream approximates zero will naturally be very indicative to the method of the invention.

The classification of the scrap glass stream thereby occurs comparing the actually acquired "UV cutoff" frequencies with material-specific reference "UV cutoff" frequencies acquired before in laboratory tests and stored in the detector unit or in the evaluation and control unit (also see illustration of the "UV cutoff" frequency in FIG. 5). Using this characteristic value, special glass pieces entrained in the scrap glass stream can be clearly recognized irrespective of their color shade and their coating thickness.

For comparing the material-specific permeability or the UV absorption or transmission values, the tangent of the UV absorption edges may be acquired and its gradient compared with stored reference. Using numerous measurement points, a transmission or absorption characteristic curve is drawn along a wavelength scale and its characteristic is compared with the characteristic of stored reference characteristic curves. Which characteristics of the transmission characteristic curve are used to clearly classify the scrap glass stream is up to the individually designed evaluation algorithms and to the respective field of application of the method. The gradient of any tangent drawn to the UV absorption edges can be acquired and compared with stored reference gradients.

In this case, to determine the intersection point of the tangent to the UV absorption edge with the abscissa (zero point of the UV absorption or transmission values) is calculated and used as a characteristic value for comparing the UV absorption or transmission values. This can be accomplished to generate a material-specific characteristic value, to draw a tangent to the UV absorption edge of the characteristic curve, to calculate the point of intersection with the abscissa of the diagram, that is to say with the wavelength scale, and to use for comparison with the permeability to UV light.

In addition, the scrap glass stream can be additionally irradiated with visible light such that special glass detection occurs by comparing the absorption or transmission values of the visible light of the scrap glass stream detected by the detector unit. The absorption or transmission values of the visible light can be obtained before from standardized material inspections. It has been found, surprisingly, that some of the special glasses have a characteristic absorption or transmission behavior in the visible range of light as well, which may also be used in this way for classification.

There can also be an apparatus for achieving the steps described above. This apparatus may be used to separate the special glass types detected in the scrap glass stream in a plurality of groups, each group being deposited on a location of its own provided for this purpose. Accordingly, diversion and sorting of detected special glasses can be performed in a plurality of fractions by means of the removal apparatus activated by the evaluation and control unit. The special glass sorting of the invention may of course also find application in combination with the sorting of streams such as common garbage, plastics or KSP (ceramics, stone and porcelain) according to prior sorting methods.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
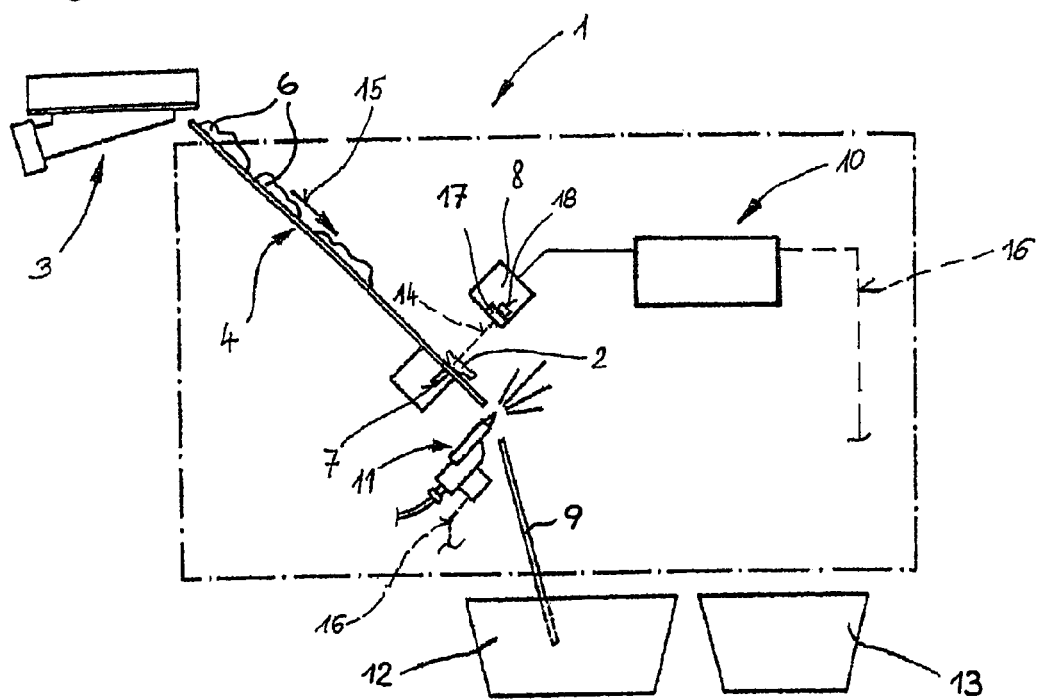
FIG. 1 shows a schematic representation of a line according to a method of the invention

FIG. 1 shows a line with a sorting chute 1 according to a method of detecting special glass, wherein this sorting chute comprises a feeder groove 3, a material chute 4, a UV radiation source 7 of the invention, a detector unit 8 together with an evaluation and control unit 10 and blowing nozzles 11 which are actuatable by means of a valve control 16, as well as at least two containers 12 and 13. A scrap glass stream 6 consisting for its major part of broken glass is automatedly forwarded in the direction of movement 15 from the feeder groove 3 through the material chute 4 into the detection range of the detector unit 8. A single piece of broken glass 2 is shown by way of example in this detection range. Depending on the classification performed by the evaluation and control unit 10 that will be described in greater detail herein after, the piece of broken glass 2 will either free-fall naturally into the container 12 of the piece fraction or be diverted during free fall by means of the blowing nozzles 11 and land in the container 13 of the scrap fraction. Deflector plates 9 are provided for more precisely forwarding the scrap glass stream into the containers 12, 13. In an alternative, the piece of broken glass 2 may also be singled out by blowing as it is being transported on a link conveyor instead of purposefully singling out by blowing free falling pieces of broken glass 2. In this context, this link conveyor is a conveying belt having appropriate apertures allowing the blowing nozzles 11 to purposefully direct their blow onto the piece of broken glass 2 and to single it out. The piece of broken glass 2 can be singled out by blowing at any angle with respect thereto or to the conveying belt.

The unwanted pieces of special glass entrained in the scrap glass stream 6 are sorted out by comparing, in accordance with the invention, the acquired UV absorption or transmission values with the stored reference values, the evaluation and control unit 10 connected to the detector unit 8 activating one or a plurality of blowing nozzles 11 disposed downstream of the detector unit 8. Instead of the blowing nozzles 11, another equivalent removal apparatus 11 such as an aspiration apparatus by means of which unwanted materials can be singled out from the scrap glass stream 6 may also be utilized.

In a preferred embodiment, the blowing nozzles 11 or other removal apparatus 11 are disposed downstream of the detector unit 8 in a plurality of separately actuatable groups in divert the special glass from the scrap glass stream 6 into a plurality of predetermined containers, thus sorting the scrap glass stream 6 into a plurality of fractions, each fraction being intended to include one specific kind of glass. In such a case, the system may have containers with three or more material fractions.

The line illustrated in FIG. 1 is merely shown by way of example and its realization, in particular the arrangement of the blowing nozzles 11 and of the containers 12 and 13, may be varied in diverse ways. Further, the conveying means for transporting the scrap glass stream 6 can be implemented as a horizontal apron conveying belt or in another way rather than in the form of a material chute 4.

Figure 2:
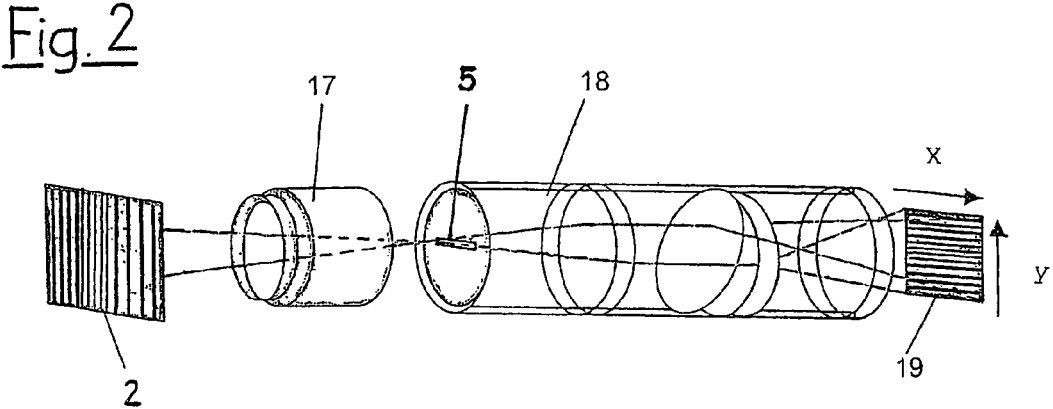
FIG. 2 shows a schematic representation of the structure of a spectrograph

To put the measurement method into practice, it is preferred to use as the detector unit 8 a space-resolving spectrometer system with an imaging UV spectrograph 18. This spectrometer system referred to as "Spectral Imaging" consists essentially, as shown in FIG. 2, of an objective lens 17, an imaging UV spectrograph 18 and a matrix detector 19 (e.g., a CCD camera). Utilizing conventional non space-resolving spectrometers, the sensing head must be caused to travel across the object or the object must be moved into different directions beneath the sensing head in order to still obtain spatially differentiated spectral information. Contrasted herewith, space-resolving spectrometer systems are measurement instruments allowing for simultaneous recording of spectral and spatial information of a surface of the object.

The detection range of the spectrograph 18 is preferably in the form of lines or strips. This is achieved in a known manner by suitably arranging the objective lenses 17 which image the radiation emitted from the scrap glass stream 6 onto the input slot 5 of the spectrograph 18. The length of the imaged strip may hereby vary from a few millimeters up to several meters, using either commercially available microscope objective lenses or current camera objective lenses. The spatial resolution varies accordingly from micrometers when the measurement is performed in the millimeter range to several millimeters if the measurement is performed in the meter range. Typically, the spectral image is taken by a monochrome CCD camera as the matrix detector 19. In a first dimension, the spatial information defined by the input slot 5, meaning the position information within a certain strip, and in a second dimension, the wavelength range to be examined is imaged. The position-dependent intensities or permeabilities can thus be illustrated for different wavelengths as a three-dimensional image. Each image point corresponds to a certain site on the imaged strip of an analyzed piece 2 and to an intensity or permeability at a certain wavelength. Usually, the spatial axis is placed in the x direction and the spectral axis in the y direction of the matrix detector 19. Then, the spatial resolution is determined by the number of image points in the x direction while the number of wavelength bands is determined by the number of image points in the y direction. Moreover, it is still necessary to move the object to be measured relative to the strip-shaped detection range in order to record a surface.

The matrix detector 19, usually a CCD camera, permits to detect either the entire UV wavelength range or only a selected portion thereof.

If material detection is not only limited to special glass but if other sorting fractions such as for porcelain or plastic material are also provided in the system, it may be necessary to utilize, in addition to the UV spectrograph 18, other spectrographs in order to also cover at need the wavelength range of visible light and of infrared light. The presence of ceramics, porcelain and stone in the scrap glass stream 6 can of course also be detected using the measurement in the live range proposed by the invention since such materials have by nature 0% light permeability or a horizontal base line 23 or 26 respectively.

Analogous data can be converted into digital data with the assistance of conventional PC-Frame Grabber cards digitizing at 8 bit, although it has been found advantageous to use resolutions of 12 to 16 bits for more complex sorting tasks. Alternatively, the analogous measurement signal can be converted into a digital signal; the need for PC-Frame Grabber cards can thereby be obviated sometimes.

In principle, it is also possible to obtain the UV absorption or transmission values of the scrap glass stream 6, not only using the transmission of the emitted UV radiation through the scrap glass stream 6 but also using the determined reflection of the UV radiation 14 impinging on the scrap glass stream 6 although such an implementation variant is more difficult to put into practice when used for glass because it is difficult to calculate the reflection and refraction effects.

In accordance with the invention, there is provided to compare UV absorption or transmission values of the scrap glass stream 6 determined by means of "Spectral Imaging" with UV absorption or transmission values obtained before from standardized material inspections. For this purpose, both singular absorption or transmission values corresponding to different wavelength measurement points can be used and corresponding material-specific transmission and absorption characteristic curves can be generated over the entire UV range or over part thereof, selected portions of these curves being compared, what are termed the UV absorption edges being compared in particular.

In spectroscopy, the absorption edge refers to the course of a transmission (which is synonym of an absorption characteristic curve) in the wavelength range in which the light irradiating the material is increasingly and finally completely absorbed, meaning that range of the absorption characteristic curve in which transmission no longer increases or absorption no longer decreases with decreasing wavelength. Depending on the composition of the material or, in the case of glass, on the chemical additives added thereto, the transmission or absorption characteristic curve has a more or less steep absorption edge, with said absorption edge dropping at different points of the wavelength scale into the range of complete impermeability, with this drop being specific to the material. Such type transmission or absorption characteristic curves are illustrated in the FIGS. 3 and 4; the absorption edge of the characteristic curve of sample 25 may thereby be recognized as that portion in which the permeability drops significantly and rapidly toward zero from the area indicated by the arrow 30.

Figure 3:
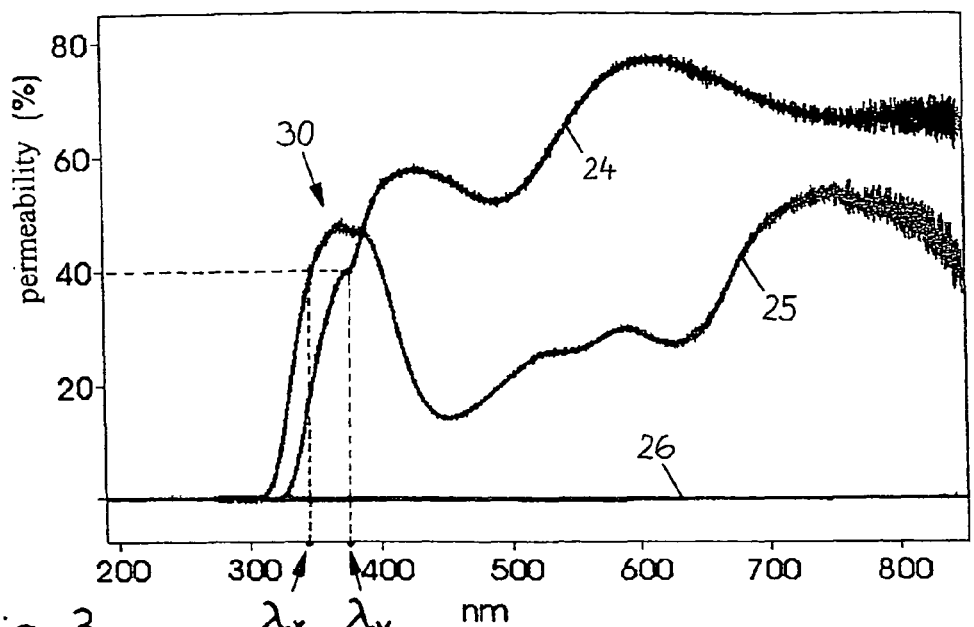
FIG. 3 shows a representation of transmission characteristic curves of three material samples in the UV/VIS range.
Figure 4:
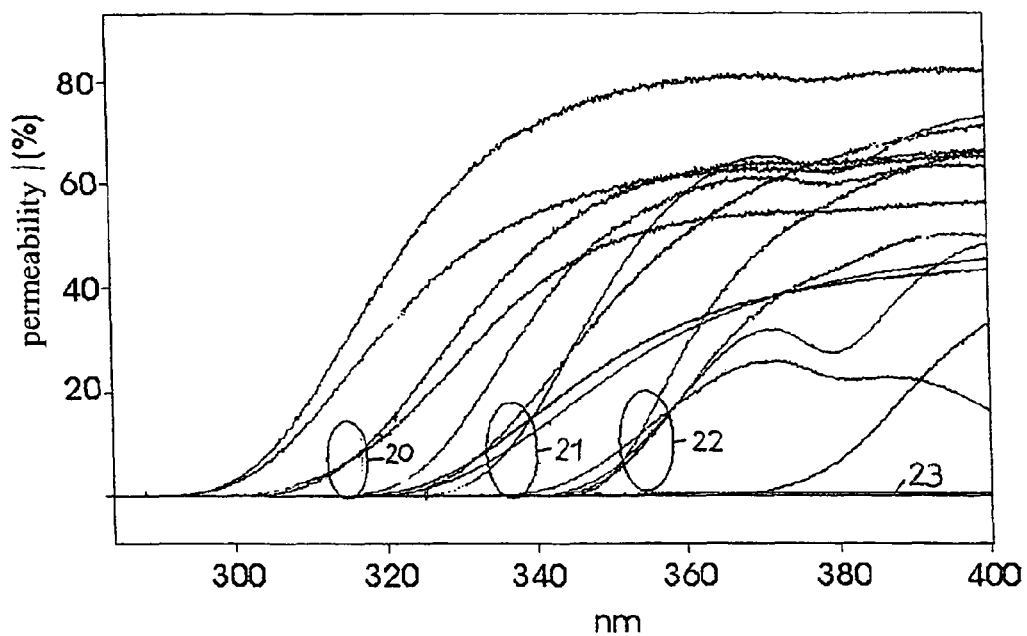
FIG. 4 shows a representation of transmission characteristic curves of a plurality of material samples in the UV range.

FIG. 3 shows the transmission characteristic curve 24, 25, 26 of three different kinds of glass, one of these samples being opaque glass-ceramics having, as a result thereof, a horizontal characteristic curve 26 oriented parallel to the abscissa. As can be seen from the courses of these transmission characteristic curves, they are not very indicative in a wavelength range outside of the UV range (from about 380 nm). The assessment of the material quality using the permeability in the range of the visible light is therefore hardly suited to detection of special glass. By contrast, the transmission characteristic curves of a plurality of glass samples obtained in a test measurement in the UV range <380 nm in accordance with FIG. 4 already allow for very clear classification in different kinds of glass. Of note is that this classification, which has been emphasized by circles 20, 21, 22 in the illustration, is now completely independent of the color and the coating thickness of the glass. Opaque samples 23 such as ceramics, stone and porcelain again will not be silhouetted against the base line and can be recognized as such by the evaluation and control unit 10.

A computer-assisted analysis of the transmission characteristic curves can be carried out using different methods. Although in principle all the claracteristic values of transmission or absorption can be used for analysis, it has been found that UV transmission or absorption values ranging from 0 to 50% are particularly well suited for detection and sorting. The characteristic value $\lambda_x$ in FIG. 3 for example corresponds to the wavelength at which 40% transmission is still measured with sample 24. By contrast, sample 25 has a wavelength of $\lambda_y$, at the same degree of transmission. These data already permit to classify the glass responsible for this measurement result for example.

Figure 5:
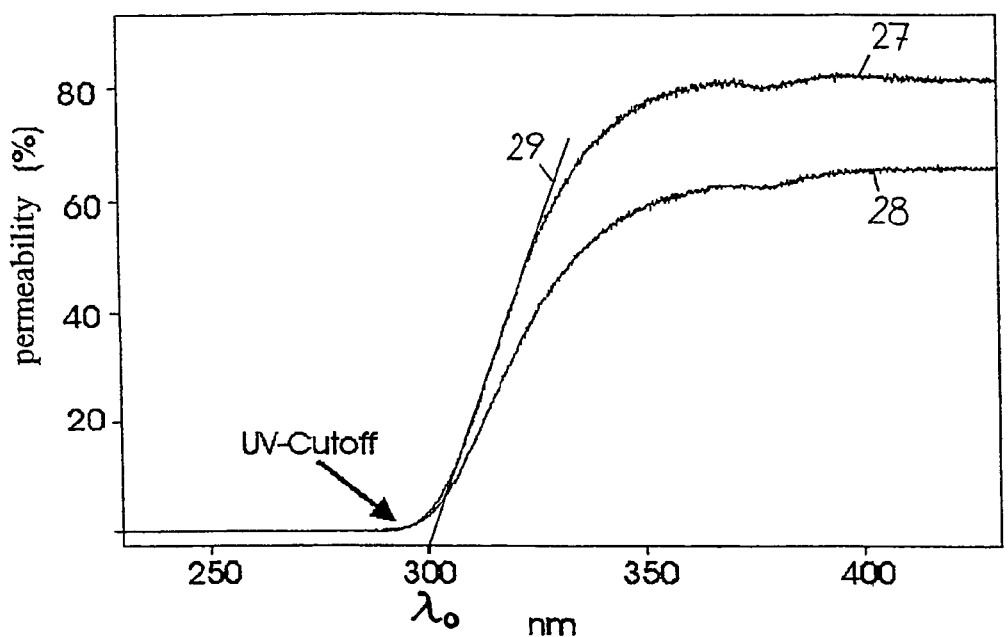
FIG. 5 shows a detailed representation of the "UV cutoff" frequency of transmission characteristic curves.

In particular the wavelength of complete absorption ("cutoff" frequency) or the wavelength range in the transition to complete absorption is particularly well suited for classifying the scrap glass stream 6 and for detection of special glass pieces entrained therein (see FIG. 5)

A method determining a tangent of the UV absorption edges and comparing its gradient with stored reference gradients for comparing these detected wavelength transition ranges with reference wavelength transition ranges has been found to be particularly advantageous. The tangent may thereby be drawn to the entire UV absorption edge, meaning to that portion of the characteristic curve from which the transmission no longer increases or the absorption no longer decreases with decreasing wavelength or on that portion of the absorption edge in which the permeability ranges between 0% and 50%.

The intersection point $\lambda_0$ of the tangent to the UV absorption edge with the abscissa can thereby be calculated and used as a characteristic value for comparing the UV absorption or transmission values. The tangent 29 shown in FIG. 5, which has been drawn to the UV absorption edge of the characteristic curve of sample 27, intersects the abscissa at a value $\lambda_0$ of 300 nm.

The samples 27, 28 are different broken pieces of the same glass. It can be seen that, although the transmission value varies over the course of the characteristic curve by virtue of the differing geometry of the samples (coating thickness, shape), the two samples show exactly the same UV absorption edge, meaning that the permeability disappears at the same wavelength. If imaginary tangents were drawn to the two absorption edges, one would again obtain from their intersection points with the abscissa characteristic values $\lambda_0$ that would also be approximately at the same wavelength.

It is understood that the tangent can be drawn to any point of the characteristic curve, for example with defined permeability values, in order to obtain different characteristic values $\lambda_0$ or gradients of the tangent for use in material analysis.

For this purpose, several measurement points of the light transmission are spaced over a defined UV wavelength range. It is practical to have the measurement points equally spaced (e.g., 30 nm) within the defined wavelength range or over the entire UV wavelength range although any spacing intervals can be chosen for their arrangement. Depending on the field of application, it may be possible, under certain circumstances, to focus the detection only onto a certain, limited wavelength range and to leave other wavelength ranges unconsidered. This permits to achieve savings in the amount of data since only selected wavelength ranges are used for actuating the removal apparatus 11 implemented as blowing nozzles mounted downstream thereof.

Although assessment of the scrap glass stream 6 using material-specific "UV-cutoff" frequencies is striking and advantageous, other indicative transmission or absorption characteristics may also be used for material analysis. The gradient of a transmission characteristic curve obtained can for example be determined at any characteristic point and compared with stored reference gradients. If a corresponding algorithm is provided to find this, other special parameters of the transmission characteristic curve in the UV wavelength range may of course also be compared with stored reference parameters.

The method of the invention may of course also be combined with known sorting methods for differentiating ceramics, stone, porcelain, plastic material or other solid materials and may thus serve to divide the inhomogeneous scrap glass stream 6 into different defined material fractions.

Additionally, there may be provided that the scrap glass stream be irradiated with visible light and that the special glass is detected by comparing the absorption or transmission values of the visible light of the scrap glass stream 6 detected by the detector unit 8 with absorption or transmission values of the visible light obtained before from standardized material inspections. As can be seen in FIG. 3 for example, some of the special glasses have a characteristic absorption or transmission behavior in the visible range of the light which may thus also be used for classification.

Accordingly, while a few embodiments of the present invention have been shown and described, it is to be understood that many changes and modifications may be made thereunto without departing from the spirit and scope of the invention as defined in the appended claims.

What is claimed is:

1. A method for detecting and sorting glass in a scrap glass stream comprising the steps of:
    emitting light rays from a radiation source in a direction traverse to the scrap glass stream wherein said light rays impinge on a detector unit;
    processing said light rays by an evaluation and control unit in data communication with said detector unit;
    activating, a removal apparatus comprising blowing nozzles disposed downstream of said detector unit, upon the detection of undesired matter in the scrap glass stream, said removal apparatus singling out undesired matter entrained in said scrap glass stream;
    diverting said undesired matter to a predetermined location, wherein said undesired matter to be detected is in the form of special glass such that the light emitted from the radiation source is in the frequency range of UV light, the special glass being detected; and
    comparing the UV absorption or transmission values of the scrap glass stream detected by the detector unit with predetermined UV absorption or transmission values obtained from standardized material laboratory inspections, the range of transmission or absorption values referred to as a UV absorption edge being used to compare the UV absorption or transmission values being the one in which transmission no longer increases or absorption no longer decreases with decreasing wavelength.

2. The method as set forth in claim 1, wherein the light emitted from the radiation source covers the entire UV wavelength range.

3. The method as set forth in claim 1, wherein the UV absorption or transmission values of the scrap glass stream detected by the detector unit are only compared in selected wavelength ranges of the UV spectrum.

4. The method as set forth in claim 1, wherein the UV absorption or transmission values of the scrap glass stream detected by the detector unit are compared in the entire wavelength range of the UV spectrum.

5. The method as set forth in claim 3, further comprising the step of providing equally spaced measurement points within the selected wavelength ranges or within the entire UV spectrum for acquiring the UV absorption or transmission values.

6. The method as set forth in claim 1 wherein the range of the UV absorption edge used for comparing the UV absorption or transmission values is that range in which the permeability of the piece from the scrap glass stream ranges from 0 to 50%.

7. The method as set forth in claim 1, wherein for comparing the UV absorption or transmission values, the tangent of the UV absorption edges is determined and its gradient is compared with stored reference gradients.

8. The method as set forth in claim 7, wherein the intersection point $\lambda_0$ of the tangent to the UV absorption edge with the abscissa or zero point of the UV absorption or transmission values is calculated and used as a characteristic value for comparing the UV absorption or transmission values.

9. The method as set forth in claim 1, further comprising the step of irradiating the scrap glass stream with visible light such that special glass detection occurs by comparing the absorption or transmission values of the visible light of the scrap glass stream detected by the detector unit with absorption or transmission values of the visible light obtained before from standardized material inspections.

10. The process as in claim 1, wherein said special glass, is selected from the group consisting of glass-ceramics, quartz glass, lead glass and temperature and heat-shock resistant technical glasses comprising borosilicate glasses.

11. An apparatus for detecting and sorting glass in a scrap glass stream, including a stream of broken glass, the apparatus comprising:
  a radiation source for emitting UV light rays in a direction traverse to a direction of said scrap glass stream;
  a detector unit for processing the light rays;
  an evaluation and control unit in communication with said detector unit;
  a removal apparatus comprising blowing nozzles disposed downstream of said detector unit, said removal apparatus being activated by said evaluation and control unit and for singling out undesired matter entrained in said scrap glass stream and diverting it to a predetermined location;
  wherein said evaluation and control unit is configured to compare the UV absorption or transmission values of the scrap glass stream detected by said detector unit with predetermined UV absorption or transmission values obtained from standardized material laboratory inspections, the range of transmission or absorption values referred to as a UV absorption edge being used to compare the UV absorption or transmission values being the one in which transmission no longer increases or absorption no longer decreases with decreasing wavelength.

12. The apparatus as set forth in claim 11, wherein said radiation source emits a light that comprises a plurality of wavelengths which cover the entire UV wavelength range.

13. The apparatus as in claim 11, wherein said evaluation and control unit is configured to evaluate special glass, which is selected from the group consisting of glass-ceramics, quartz glass, lead glass and temperature and heat-shock resistant technical glasses comprising borosilicate glasses.

14. A method for detecting and sorting glass in a scrap glass stream comprising the steps of:
  emitting light rays from a radiation source in a direction traverse to the scrap glass stream wherein said light rays impinge on a detector unit;
  processing said light rays by an evaluation and control unit in data communication with said detector unit;
  comparing the UV absorption or transmission values of the scrap glass stream detected by the detector unit with predetermined UV absorption or transmission values obtained from standardized material laboratory inspections, the range of transmission or absorption values referred to as a UV absorption edge being used to compare the UV absorption or transmission values being the one in which transmission no longer increases or absorption no longer decreases with decreasing wavelength;
  diverting said undesired matter to a predetermined location, wherein said undesired matter to be detected is in the form of special glass such that the light emitted from the radiation source is in the frequency range of UV light, the special glass being detected; and
  activating, a removal apparatus comprising blowing nozzles disposed downstream of said detector unit, upon the detection of undesired matter in the scrap glass stream, said removal apparatus singling out undesired matter entrained in said scrap glass stream wherein the undesired material is filtered out based upon the wavelength detected at which the permeability of the undesired material approximates zero.

15. The process as in claim 14, wherein said wavelength is determined by acquiring a tangent of an absorption edge.

16. The process as in claim 14, further comprising the step of storing in a detector unit a plurality of UV cutoff frequencies acquired prior to the step of comparing the UV absorption or transmission values.

17. The method as in claim 14, wherein the light emitted from the radiation source comprises as plurality of wavelengths which cover the entire UV wavelength range.

* * * * *